United States Patent [19]
Xu

[11] Patent Number: 5,492,823
[45] Date of Patent: Feb. 20, 1996

[54] **METHOD FOR DIRECT CLONING AND PRODUCING THE BSOBI RESTRICTION ENDONUCLEASE IN *E. COLI***

[75] Inventor: Shuang-yong Xu, Lexington, Mass.

[73] Assignee: New England Biolabs, Inc., Beverly, Mass.

[21] Appl. No.: 356,898

[22] Filed: Dec. 15, 1994

Related U.S. Application Data

[63] Continuation-in-part of Ser. No. 247,990, May 24, 1994.
[51] Int. Cl.$^6$ .............................. C12N 9/22; C12N 15/55
[52] U.S. Cl. ..................... 435/199; 435/193; 435/320.1; 435/252.33; 536/23.2
[58] Field of Search .................................. 435/199, 193, 435/320.1, 252.33; 536/23.2

[56] References Cited

U.S. PATENT DOCUMENTS 5,200,333  3/1981  Wilson .

OTHER PUBLICATIONS

Kosykh, et al., Molec. Gene. Genet. 178:717–718 (1980).
Mann, et al., Gene, 3:97–112 (1978).
Walder, et al., Proc. Natl. Acad. Sci. USA, 78:1503–1507 (1981).
Bougueleret, et al., Nucl. Acid. Res., 12:3659–3676 (1984).
Gingeras and Brooks, Proc. Natl. Acad. Sci. USA, 80:402–406 (1983).
Theriault and Roy, Gene, 19:355–359 (1982).
Blumenthal, et al., J. Bacteriol., 164:501–509 (1985).
Kiss, et al., Nucl. Acid. Res., 13:6403–6421 (1985).
Szomolanyi, et al., Gene, 10:219–225 (1980).
Janulaitis, et al., Gene, 20:197–204 (1982).
Kiss and Baldauf, Gene, 21:111–119 (1983).
Walder, et al., J. Biol. Chem., 258:1235–1241 (1983).
Raleigh and Wilson, Proc. Natl. Acad. Sci. USA, 83:9070–9074 (1986).
Kelleher and Raleigh, J. Bacteriol. 173:5220–5223 (1991).
Kenyon and Walker, Proc. Natl. Acad. Sci. USA, 77:2819–2823 (1980).
Heitman and Model, J. Bacteriol., 169:3234–3250 (1989).
Pierkarowicz, et al., J. Bacteriol. 173:150–155 (1991).
Panayotatos and Fontaine, J. Biol. Chem., 260:3173–3177 (1985).
Xu and Schildkraut, J. Biol., Chem., 266:4425–4429 (1991).
Iwaski, et al., J. Bacteriol., 172:6268–6273 (1990).
L. K. Lewis, J. Bacteriol., 174:5110–5116 (1992).
Hoffman, et al., Proc. Natl. Acad. Sci., 82:5107–5111 (1985).
Engebrecht, Science, 227:1345–1347 (1985).
Metcalfe, Gene, 129:17–25 (1993).
Ward, et al., Mol. Gen. Genet., 203:468–478 (1986).
Bingle, et al., Can. J. Microb. 39:70–80 (1993).
Fomenkov, A., et al. (1994) Nucl. Acids Res. 22(12), 2399–2403.
Piekarowicz, A., et al. (1991) Nucl. Acids Res. 19(8), 1831–1835.
Heitman, J., et al. (1991) Gene 103, 1–9.

*Primary Examiner*—Charles L. Patterson, Jr.
*Attorney, Agent, or Firm*—Gregory D. Williams

[57] ABSTRACT

The present invention discloses a novel method for the direct cloning of nuclease genes such as restriction endonuclease genes in E. coli. In addition, there is provided a novel strain which facilitates application of the method. This method has been successfully employed to clone a number of genes coding for endonuclease including restriction endonuclease genes.

5 Claims, 4 Drawing Sheets

5,492,823

METHOD FOR DIRECT CLONING AND PRODUCING THE BSOBI RESTRICTION ENDONUCLEASE IN E. COLI

This is a continuation-in-part of application(s) Ser. No. 08/247,990 filed on May 24, 1994.

BACKGROUND OF THE INVENTION

The present invention relates to recombinant DNA which encodes the BsoBI restriction endonuclease, as well as to related methods for over-expressing this recombinant enzyme.

Nucleases are a class of enzymes which degrade or cut single- or double-stranded DNA. Restriction endonucleases are an important class of nucleases which recognize and bind to particular sequences of nucleotides (the 'recognition sequence') along the DNA molecule. Once bound, they cleave both strands of the molecule within, or to one side of, the recognition sequence. Different restriction endonucleases recognize different recognition sequences. Over one hundred and eighty restriction endonucleases with unique specificities have been identified among the many hundreds of bacterial species that have been examined to date.

It is thought that in nature, restriction endonucleases play a protective role in the welfare of the bacterial cell. They enable bacteda to resist infection by foreign DNA molecules like viruses and plasmids that would otherwise destroy or parasitize them. They impart resistance by cleaving invading foreign DNA molecules when the appropriate recognition sequence is present. The cleavage that takes place disables many of the infecting genes and renders the DNA susceptible to further degradation by non-specific endonucleases.

A second component of these bacterial protective systems are the modification methylases. These enzymes are complementary to the restriction endonucleases and they provide the means by which bacteria are able to protect their own DNA from cleavage and distinguish it from foreign, infecting DNA. Modification methylases recognize and bind to the same nucleotide recognition sequence as the corresponding restriction endonuclease, but instead of cleaving the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified by virtue of the activity of the modification methylase. It is therefore completely insensitive to the presence of the endogenous restriction endonuclease. It is only unmodified, and therefore identifiably foreign DNA, that is sensitive to restriction endonuclease recognition and cleavage.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e., populations of clones derived by 'shotgun' procedures, when they occur at frequencies as low as $10^{-3}$ to $10^{-4}$.

Type II restriction-modification systems are being cloned with increasing frequency. The first cloned systems used bacteriophage infection as a means of identifying or selecting restriction endonuclease clones (EcoRll: Kosykh et al., Molec. Gen. Genet. 178:717–719, (1980); Hhall: Mann et al., Gene 3:97-112, (1978); Pst I Walder et al., Proc. Nat. Acad. Sci. 78:1503–1507, (1981)). Since the presence of restriction-modification systems in bacteria enables them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into E. coli cloning plasmids (EcoRV: Bougueleret et aL, Nucl. Acid. Res. 12: 3659–3676, (1984); PaeR7: Gingeras and Brooks, Proc. Natl. Acad. Sci. USA 80:402–406, (1983); Theriault and Roy, Gene 19:355–359 (1982); Pvull: Blumenthal et al., J. Bacteriol. 164:501–509, (1985)).

A third approach, and one that is being used to clone a growing number of systems are now being cloned by selection for an active methylase gene. See, e.g., U.S. Pat. No. 5,200,333, and Bsu Rl: Kiss et al., Nucl. Add. Res. 13: 6403–6421, (1985)). Since restriction and modification genes are often closely linked, both genes can often be cloned simultaneously. This selection does not always yield a complete restriction system however, but instead yields only the methylase gene (BspRl: Szomolanyi et al., Gene 10: 219–225, (1980); Bcnl: Janulaitis et al, Gene 20:197–204 (1982); BsuRl: Kiss and Baldauf, Gene 21: 111–119, (1983); and Mspl: Walder et al., J. Biol. Chem. 258: 1235–1241, (1983)).

A fourth cloning method (the "methylase indicator" method) relies on methylation-dependent restriction systems McrA, McrBC, and Mrr (Raleigh and Wilson, Proc. Natl. Acad. Sci., USA 83: 9070–9074, (1986), Heitman and Model, Gene. 103:1–9 (1991); Kelleher and Raleigh, J. Bacteriol. 173:5220–5223, (1991)) and the dinD1::lacZ operon fusion to screen for clones that contain methylase genes. The dinD1 locus is a DNA damage inducible gene that is expressed in E. coli when the "SOS response" is triggered, as by UV treatment, mitomycin treatment, or the action of McrA, McrBC, or Mrr restriction endonucleases on methylated DNA (Kenyon and Walker, Proc. Natl. Acad. Sci. USA, 77:2819–2823, (1980), Heitman and Model, Gene, 103:1–9, (1991); Heitman and Model, J. Bacteriol. 169:3234–3250, (1989); and Piekarowicz et al. J. Bacteriol. 173:150–155, (1991), the disclosures of which are incorporated herein by reference). Strains with temperature-sensitive mutations in mcrA, mcrBC, mrr and carrying the dinD1 ::lacZ fusion were constructed and used for the direct cloning of methylase genes into E. coli from other bacterial sources (Piekarowicz etal., Nucleic Acids Res. 19:1831–1835, (1991), the disclosure of which is incorporated herein by reference). Upon transformation of ligated genomic/vector DNA into such strains, transformants containing a gene expressing a methylase that confers sensitivity to one of the methylation-dependent restriction systems form white colonies at 42° C. and blue colonies at 30° C. on X-gal indicator plates as a result of methylation-dependent restriction that results in SOS DNA repair induction and β-galactosidase expression. Because of close linkage between most restriction enzyme genes and the cognate methylase genes, cloning of a methylase gene in a DNA fragment of reasonable size may lead to concomitant cloning of the cognate endonuclease gene.

It would be desirable to design a method for the direct cloning of nucleases, such as the BsoBl restriction endonucleases, as an alternative method when standard approaches are either impractical or fail to yield positive results.

SUMMARY OF THE INVENTION

In accordance with the present invention, a novel method for the direct cloning of nuclease genes such as BsoBl restriction endonuclease genes in *E. coli* is provided. This method has been successfully employed to clone a number of genes coding for nucleases including restriction endonuclease genes such as BsoBl from Bacillus stearothermophilus. Accordingly, there is also provided isolated DNA which encodes bsoBIR gene, as well as vectors, transformed host cells for expressing BsoBl.

More specifically, the present invention employs (i) an *E. coli* strain containing the dinD1::lacZ fusion, which is deficient in all restriction systems (EcoKR$^-$, McrA$^-$, McrBC$^-$, Mrr$^-$), (ii) a method for direct cloning of the BsoBl endonuclease gene in *E. coli* using a strain which contains a fusion of a DNA damage-inducing promoter and an indicator/reporter gene such as the dinD1::lacZ fusion, and (iii) isolated DNA coding for BsoBl cloned by this method. As it has been shown that DNA breaks or nicks introduced by the T7.3 endonuclease, EcoRl, or BamHl restriction enzymes induce the SOS response in E. coli. (Panayotatos and Fontaine, J. BioL Chem. 260:3173–3177, (1985), Heitman and Model, Gene, 103:1–9, (1991), Xu and Schildkraut, J. Biol. Chem. 266:4425–4429, (1991)), the present inventor reasoned that when ligated genomic DNA fragments and vector are introduced into an indicator strain such as dinD1::lacZ deficient in all restriction systems so far described and transformants plated on X-gal plates, one might find the nuclease-containing clone directly by picking blue colonies. When used to clone genes coding for a restriction endonuclease, unlike the methylase selection approach, it is not necessary that the methylase gene fully protect the host chromosome. In fact, the methylase gene may be absent altogether. This is particularly true for thermostable enzymes such as BsoBl where, in accordance with the present invention, the transformants are grown at lower temperatures, i.e., between about 30°–37° C. At this lower temperature, thermostable restriction endonucleases are less active, and transformed host cells may survive with partial or even without protective methylation.

In other words, in accordance with the method of the present invention, when host cells such as the preferred *E. coli* cells (dinD1::lacZ, EcoKR$^-$, McrA$^-$, McrBC$^-$, Mrr$^-$) are transformed with ligated genomic/vector DNA and transformants are plated on X-gal plates, cells carrying the restriction endonuclease gene form blue colonies because the restriction enzyme damages DNA in vivo and induces the SOS DNA repair response. This method (the "endo-blue method") differs from the "methylase indicator method", Piekarowicz et al.,supra, in that the earlier method detected expression of the methylase, not the endonuclease. That method relied on the DNA-damaging action of endogenous restriction enzymes (McrA, McrBC or Mrr) that act on specific methylated sequences. Expression of an appropriate foreign methylase can create a sequence susceptible to one or more of these methylation-specific endonucleases, leading to SOS-induction and blue color. The gene for the cognate endonuclease might or might not accompany the methylase gene. The "endo-blue method" of the present invention detects the endonuclease only and not the methylase, because the relevant methylation-dependent restriction systems are absent from the host. The genes coding for the thermostable restriction enzymes BsoBl (5'CPyCGPuG3'), Taql (5'TCGA3') and Tth111l (5'GACNNNGTC3') have been successfully cloned in *E. coli* by this method. The methylase selection method (Szomolanyi et al. Gene 10: 219–225, (1980) and the "endo-blue method" can also be combined to clone restriction endonuclease genes. The gene coding for the restriction endonuclease ecoO109lR has been cloned by combining these two methods.

DETAILED DESCRIPTION OF THE INVENTION

Figure 1:
FIG. 1 shows BsoBl activity assay. One μg of lambda DNA substrate was incubated with 10 μl of cell extract at 65° C. for one hour in buffer containing 50mM NaCl, 10 mM Tris-HCl, 10 mM MgCl$_2$, 1 mM DTT. The digested DNA products were resolved in an 0.8% agarose gel and detected by ethidium bromide staining. The cell extract from isolate #16 was found to contain BsoBl endonuclease activity. First lane: BsoBl positive control. The number above each lane indicates isolate number.

In accordance with one embodiment of the invention, there is provided isolated DNA, vectors transferred to host cells as well as a novel method for the direct cloning of BsoBl. In general, the method comprises the following steps, although as the skilled artisan will appreciate, modifications to these steps may be made without adversely affecting the outcome:

1) Genomic DNA is prepared from the BsoBl producing strain and cleaved completely or partially to generate about 1000 bp –20,000 bp clonable DNA fragments. These fragments may be obtained, for example, with restriction enzymes or sheared by sonication. The fragments so obtained are thereafter ligated to cloning vectors with compatible cohesive ends or blunt ends in pBR322, pUC19, pACYC187, pSC101, or their derivatives.

2) The ligated DNA mixture is transferred into a bacterial strain which contains a DNA damage-producing promoter fused to an indicator/reporter such as the preferred dinD-::lacZ fusion and which is deficient in methylation-dependent restriction systems (dinD::lacZ, hsdR, mcrA, mcrBC, mrr). One preferred strain is *E. coli* ER1992 (NEB #907), a sample of which has been deposited at the American Type Culture Collection under the terms of the Budapest Treaty on May 24, 1994, ATCC Accession No. 55582. Other DNA damage-inducing promoters which can be used include dinA (Iwasaki, M., et al., J. Bacteriol., 172:6268–6273 (1990) and dinG (Lewis, L.K., J. Bacteriol 174:5110–5116 (1992), the disclosures of which are incorporated herein by reference. Other indicator/reporter genes which can be fused to any of the above promoters include alkaline phosphatase (phoA) (Proc. Natl. Acad. Sci. USA, 82:5107–5111 (1985), luciferase (lux) (Engelrecht, J., Science, 227:1345–1347 (1985), β-glucuronidase (Metcalfe, W. W., Gene, 129:17–25 (1993), aminoglycoside phosphotransferase (Ward, J. M., et al, Mol Gen. Genet., 203:468–478 (1986), and endoglucanase (Bingle, W. W., et al, Can. J. Microbiol., 39:70–80

(1993), the disclosures of which are incorporated herein by reference.

After transformation into *E. coli* ER1992, the cells are plated on indicator plates containing X-gal and appropriate antibiotics and incubated overnight at about 30° C. to 42° C. Sometimes none of or not all of the methylation-dependent restriction systems of the host have to be inactivated depending on the particular restriction endonuclease gene or nuclease genes to be cloned. While total deficiency in these systems is not required, it is preferable to use the dinD::lacZ strains deficient in all the methylation-dependent systems to clone a restriction-modification system if one does not know the modified bases (unusually $C^5$ cytosine, $N^4$ cytosine, or $N^6$ adenine).

3) Individual medium/dark blue colonies are picked and inoculated into LB media plus the appropriate antibiotics (10 ml to 1000 ml) and shaken overnight at about 30° C. to 42° C.

4) Cells are harvested by centrifugation, resuspended in sonication buffer plus lysozyme and cell lysis is completed by sonication. Cell debris and insoluble components are removed by centrifugation.

5) Where, as for BsoBl, the nuclease gene to be cloned is from a thermostable bacterium, the lysate is heated at about 65° C. for a period of time (for example 30 min) sufficient to denature *E. coli* native proteins. This step efficiently inactivates native *E. coli* nucleases.

6) The supernatant (cell extract) is assayed for nuclease activity on appropriate DNA substrates such as pUC19, pBR322, M13mp18/19 replicarive form or single-stranded DNA or λ DNA at 37° C. to 68° C. in an appropriate buffer.

7) DNA digestion patterns or fragments are resolved by agarose gel electrophoresis or PAGE and detected by ethidium bromide staining.

This method has been successfully used to clone the thermostable endonuclease including BsoBl from *Bacillus stearothermophilus* (NEB #882). BsoBl is an isoschizomer of Ava 1 which recognizes CPyCGPuG. This method has also been successfully used to clone a number of nuclease genes including the taql R gene, the tth111lR gene, as well as the gene coding for the Thermus nuclease from *Thermus filiformus*.

As noted above, the present invention employs a novel stain which can be used in the above-described "endo-blue method", This stain, E. coli ER1992, contains the dinD::lacZ fusion and is deficient in all restriction systems (EcoKR⁻, McrA⁻, McrBC⁻ and Mrr⁻).

E coli ER1992 (F-λ-Δ(argF-lac)U169 supE44 e14⁻ dinD1::Mu dl1734 (Kan', LacZ⁺)rfbD1? relA1? endA1 spoT1?thi-1 Δ(mcrC-mrr)114::IS10) was constructed in three steps: (i) A Lac⁻ derivative of ER1821 was obtained by transduction with a proC::Tn5 linked to Δ(argF-lac)U169 from NK6993, selecting for Kan' and screening for Lac⁻ Pro⁻ to yield ER1984; (ii) this derivative was made Pro⁺ Kan' by transduction from ER1578, yielding ER1991; (iii) dinD1::Mu dl1734(Kan', LacZ⁺) was introduced by transduction from JH140, (an *E. coli* strain which is dinD1::Mu dl1734 (Kan', LacZ⁺) (J. Heitman, et aL, Gene 103:1–9 (1991)) selecting KanR and screening for nalidixic acid-inducible expression of β-galactosidase mediated by the dinD fusion. This was tested on X-gal plates with a central well containing this DNA-damaging agent. Purified transductants were streaked radially from the well. One that yielded a gradient of dark blue color was designated *E. coli* ER1992. This strain showed light blue color on X-gal in the absence of any DNA damage.

The following examples are given to illustrate embodiments of the present invention as it is presently preferred to practice. It will be understood that these examples are illustrative, and that the invention is not to be considered as restricted thereto except as indicated in the appended claims.

EXAMPLE 1

CLONING OF THE bsoBIR GENE CODING FROM THE BsoBl

RESTRICTION ENDONUCLEASE IN *E. coli*

Bacterial DNA purification: Five grams of *Bacillus stearothermophilus* (NEB#882) cells were resuspended in 25 ml of buffer containing 25% sucrose, 50 mM Tris-HCl, pH 8.0. Five ml of 0.5 M EDTA, pH 8.0, and 6 ml of lysozyme (10 mg/ml) were added to the cell suspension. After 10 mm incubation at room temperature, 36 ml of lysis buffer (1% Triton X-100, 50 mM Tris-HCl, pH 8.0, 62 mM EDTA) and 5 ml of 10% SDS were added to completely lyse the cells. Proteins were removed by phenol-$CH_3Cl$ extraction twice and $CH_3Cl$ extraction twice. Genomic DNA was precipitated by addition of ⅒ volume of 3.5 M sodium acetate and equal volume of isopropanol and centrifugation at 15,000 g. The DNA pellet was washed with 50 ml of 70% ethanol and dried under vacuum. The DNA pellet was resuspended in 10 ml of TE buffer and dialysed in 2 liters of TE buffer (10 mM Tris-HCl, pH 7.8, 1 mM EDTA) overnight at 4° C.

Partial digestion of genomic DNA: Fifty μg of genomic DNA was digested with 2 units, 1 unit, 0.5 unit, 0.25 unit, 0.125 unit of Sau3Al respectively at 37° C. for 30 min. The digested DNA was purified by phenol-$CH_3Cl$ extraction twice and $CH_3Cl$ extraction twice and ethanol precipitation. Vector pUC19 DNA was linearized by Barnill restriction enzyme and dephosphorylated by calf intestinal alkaline phosphatase (CIP). After CIP treatment, the vector DNA was purified by phenol-$CH_3Cl$ extraction twice and $CH_3Cl$ extraction twice and ethanol precipitation.

Ligation and transformation: Ten μg of Sau3Al partially digested genomic DNA was ligated with 1 μg BamHl-cleaved and CIP-treated pUC19 DNA at 16° C. overnight. The ligated DNA was diluted with addition of equal volume of TE buffer and used to transform ER1992 (dinD1::lacZ⁺, hsdR, mcrA, mcrBC, mrr) competent cells. Transformants were plated on Ampicillin (Ap) plus X-gal plates (5-bromo-4-chloro-3-indolyI-D-galactopyranoside, X-gal, 0.16 mg/ml) and incubated at 37° C. overnight. Twenty-four blue colonies were found among 10,000 transformants and each blue colony inoculated into 10 ml LB plus Ap and incubated overnight at 37° C. in a shaker. Cells were harvested by centrifugation and resuspended in 1 ml of sonication buffer (10 mM Tris-HCl, pH 7.8, 10 mM β-mercaptoethanol, 10 mg/ml lysozyme). Cell lysis was completed by sonication twice, each time for 30 seconds. Insoluble components were removed by centrifugation and the supernatant was collected and used for endonuclease activity assay as follows: 1 μg of lambda DNA substrate was incubated with 10 μl of cell extract at 65° C. for one hour in a buffer containing 50 mM NaCl, 10 mM Tds-HCl, 10 mM $MgCl_2$, 1 mM DTT. DNA fragments were resolved in an 0.8% agarose gel and detected by ethidium bromide staining. The cell extract from one isolate was found to contain BsoBl endonuclease activity (see FIG. 1, isolate #16). Plasmid DNA was extracted from this strain and digested with BsoBl restriction endonuclease to check resistance. The plasmid DNA was cleaved by BsoBI, indicating that either the BsoBI methylase gene is not present in the insert or the methylase gene is not expressed at all. The plasmid carrying the BsoBI endonuclease gene (BsoBIR) was named pBsoR1. To determine the stability of BsoBI clone, ER1992 [pBsoR1] cells were grown at 37° C. and plasmid DNA was isolated from the cells and used to retransform into ER1992 competent cells. In the retransformation experiment, transformants were plated at 30° C. to minimize further mutations. It was found that 67% transformants form blue colonies (356 blue colonies out of 528 transformants), while the other 33% form white colonies (172 white colonies out of 528 transformants). When plasmid DNA was isolated from the white colonies and analyzed by restriction digestion, it was found that the DNA showed extensive deletions. It was concluded that ER1992 [pBsoR1] cells are not very stable at 37° C. ER1992 [pBsoR1] cells are more stable when the blue colony carrying pBsoR1 was incubated overnight at 30° C. instead of 37° C. When plasmid DNA isolated from the 30° C. culture was used for the retransformation, 99.6% of the transformants form blue colonies at 30° C. (480 blue colonies, 2 white colonies). A sample of pBsoR1 (NEB#951) has been deposited under the terms of the Budapest Treaty at the American Type Culture Collection on Dec. 13, 1994, and received ATCC Accession No. 75966.

The genes coding for the AvaI restriction-modification system has been cloned at New England Biolabs. AvaI and BsoBI share the same recognition sequence 5'CPyCGPuG3'. A 1.8 kb PstI fragment carrying the AvaI methylase gene (avaIM) was digested from pAvaIRM12 and cloned into the pR976 vector (a pACYC184 derivative, TcR). The plasmid pR976-avaIM was transformed into ER1992 (dinD1::LacZ) cells to premodify the *E. coli* chromosome. A second plasmid, pBsoR1, carrying the BsoBI endonuclease gene, was then introduced into the cells containing pR976-avaIM and plated on X-gal indicator plate. It was found that the transformants still form blue colonies, indicating the AvaI methylase does not protect *E. coli* chromosome against BsoBI endonuclease damage.

Plasmid mini-preparation procedure: 1.5 ml overnight culture was pelleted for 3 minutes. The supernatant was poured off and the cell pellet was resuspended in 200 ml STET buffer (50 mM Tds-HCl, pH 7.8, 50 mM EDTA, 0.5% Triton-X100, 8% sucrose). 50 μl of lysozyme (10 mg/ml) was added to the cell suspension. The lysed cells were boiled for 1 min in boiling water and the precipitate was spun down at 14,000xg, for 10 minutes. 200 μl supernatant was collected and mixed with 100 μl 7.5 M NH3Ac and 600 ml isopropanol. DNA was precipitated by centrifugation at 14,000xg for 10 minutes at room temperature. The DNA pellet was washed with 1 ml of 70% ethanol, and dried for 15 minutes under vacuum. Once dry, the pellet was resuspended in 100 μl of TE buffer plus 5 μl of RNaseA (10 mg/ml).

Figure 2:
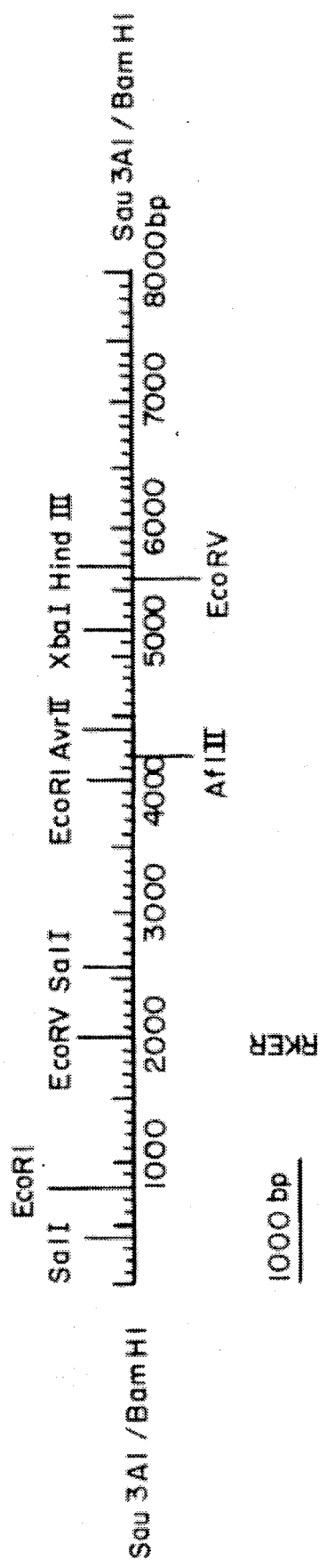
FIG. 2 is a restriction map of the DNA insert containing the BsoBl restriction endonuclease gene. The insert size is approximately 8.1 kb. The insert was derived from Sau3Al partially-digested *Bacillus stearothermophilus* genomic DNA and cloned into the BarnIll site of pUC19.

Restriction mapping of the insert: The plasmid DNA pBsoR1 was digested with various restriction enzymes and the digested DNA products were analyzed by agarose gel electrophoresis. The restriction map was shown in FIG. 2.

EXAMPLE 2

CLONING OF TAQI R GENE IN E. COLI

Bacterial DNA purification was done as follows: Five grams of *Thermus aquaticus* YT-1 (ATCC 25104) cells were resuspended in 25 ml of buffer containing 25% sucrose, 50 mM Tris-HCl, pH 8.0. Five ml of 0.5 M EDTA, pH 8.0, and 6 ml of lysozyme (10 mg/ml) were added to the cell suspension. After 10 min incubation at room temperature, 36 ml of lysis buffer (1% Triton X-100, 50 mM Tris-HCl, pH 8.0, 62 mM EDTA) and 5 ml of 10% SDS were added to completely lyse the cells. Proteins were removed by phenol-$CHCl_3$ extraction twice and $CHCl_3$ extraction twice and genomic DNA was precipitated by addition of 1/10 volume of 3.5 M sodium acetate and equal volume of isopropanol and centrifugation at 15,000 g. The DNA pellet was washed with 50 ml of 70% ethanol and dried under vacuum. The DNA was resuspended in 10 ml of TE buffer and dialysed in 2 liters of TE buffer overnight at 4° C. Fifty μg of genomic DNA was digested with 1 unit, 0.5 unit, 0.25 unit, 0.125 unit of Sau3AI at 37° C. for 30 min. The digested DNA was purified by phenol-$CHCl_3$ extraction twice and $CHCl_3$ extraction twice and ethanol precipitation. Vector pBR322 DNA was linearized by Bam HI restriction enzyme and dephosphorylated by calf intestinal alkaline phosphatase (CIP). The vector DNA was purified again by phenol-$CHCl_3$ extraction twice and $CHCl_3$ extraction twice and ethanol precipitation.

Figure 4:
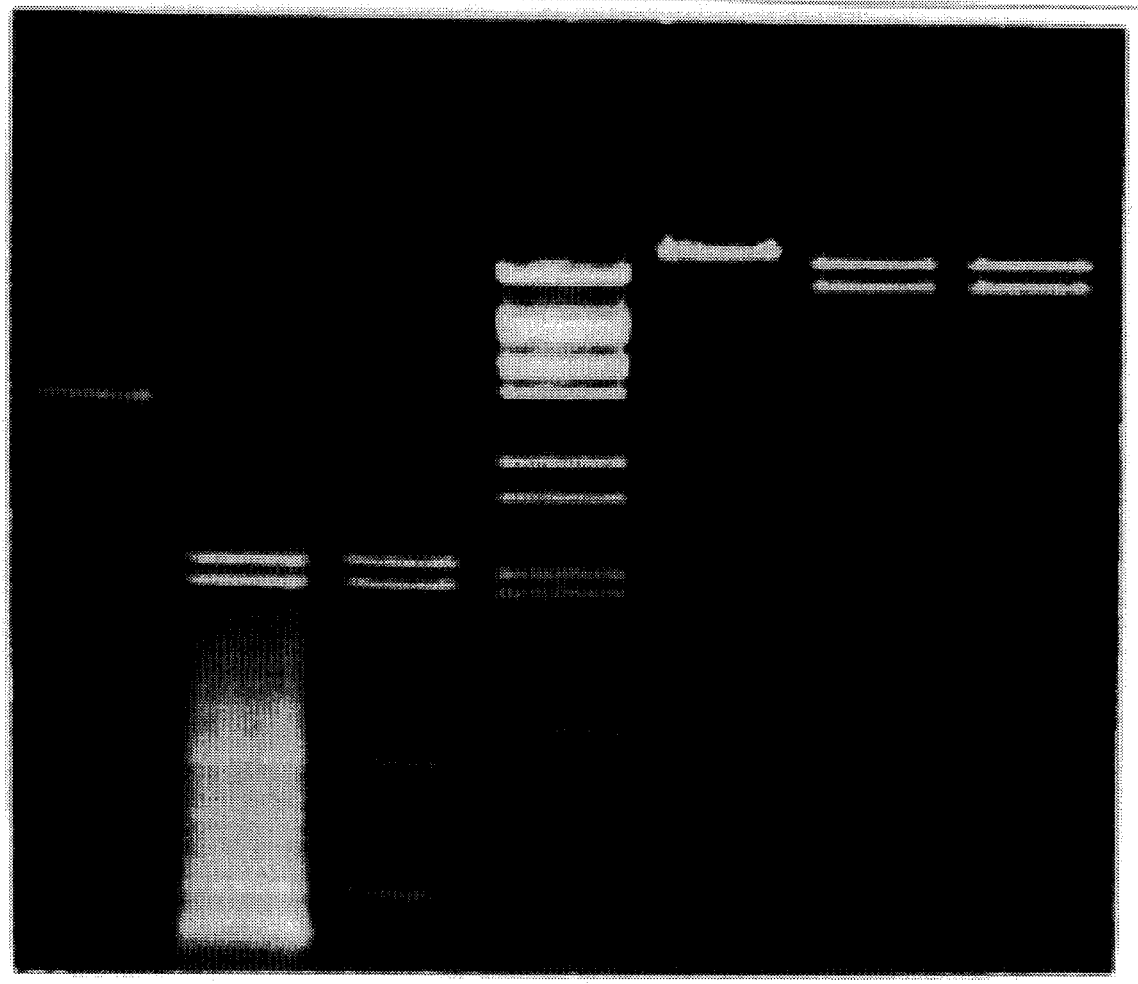
FIG. 4 shows the DNA cleavage pattern produced by cloned Taql and Tth 111l restriction enzymes produced in E. coli.

The Sau3AI partially digested genomic DNA was ligated with BamHI-cleaved and CIP-treated pBR322 DNA. A total of 4,000 colonies were obtained from one transformation experiment by mixing *E. coli* ER1992 (dinD1::lacZ, hsdR, mcrA, mcrBC, mrr) competent cells and the ligated DNA and transformants are plated on Ap plus X-gal plates (5-bromo-4-chloro-3-indolyl-D-galactopyranoside, X-gal, 0.16 mg/ml). Ten blue colonies were found and each inoculated into 10 ml LB plus Ap and incubated overnight at 37° C. in a shaker. Cells were harvested by centrifugation and resuspended in 1 ml of sonication buffer (10 mM Tris-HCl, pH 7.8, 10 mM β-mercaptoethanol) plus lysozyme (10 mg/ml). Cell lysis was completed by sonication. E coli proteins were heat-denatured by incubation of lysate at 65° C. for 30 min. Insoluble components were removed by centrifugation and the supernatant was used for endonuclease activity assay. λ or pBR322 DNA substrates were incubated with 5 μl of cell extract at 65° C. for one hour. DNA fragments were resolved in 0.8% agarose gels and detected by ethidium bromide staining. When cell extracts were examined for endonuclease activity on pBR322 substrate, two strains were found to make TaqI endonuclease (FIG. 4). Plasmid DNA was extracted from these two strains and subjected to TaqI endonuclease digestion. One plasmid was partially resistant to TaqI digestion and the other was completely digested. It was inferred from the above result that one clone contains TaqI methylase gene and the second clone may not.

Plasmid mini-preparation procedure: 1.5 ml overnight culture was pelleted for 3 minutes. The supernatant was poured off and the cell pellet was resuspended in 200 μl STET buffer (50 mM Tris-HCl, pH 7.8, 50 mM EDTA, 0.5% Triton-X100, 8% sucrose). 50 μl of lysozyme (10 mg/ml) was added to the cell suspension. The lysed cells were boiled for 1 min in boiling water and the precipitate was spun down at 14,000xg, for 10 minutes. The supernatant was removed and extracted with an equal volume of phenol/chloroform (1:1). The layers were separated by centrifugation at 14,000xg for five minutes. The upper phase was taken into a new centrifuge tube and extracted with equal volume of chloroform. The DNA was mixed with 1/10 volume of sodium acetate and equal volume of isopropanol. The tube was spun at 14,000xg for 10 minutes to pellet the precipitated nucleic acids. The supernatant was discarded and the pellet was washed with 1 ml of 70% ethanol, repelleted and dried for 15 minutes under vacuum. Once dry, the pellet was resuspended in 100 μl of TE buffer (10 mM Tris-HCl, 1 mM EDTA, pH 8.0).

To estimate TaqI endonuclease yield one liter cell culture was made at 37° C. and cell extract assayed for activity. Both strains make about $5\times10^4$ units of TaqI per gram of wet cells. Cell extract was prepared as follows: 1 liter of LB plus Ap was inoculated with 5 ml of overnight cells and shaken at 37° C. overnight. The cells were centrifuged and cell pellet resuspended in 20 ml sonication buffer (10 mM Tris-HCl, 10 mM β-mercaptoethanol), sonicated for ten times at 30 seconds burst, centrifuged at 15000xg for 30 minutes to remove cell debris. The supernatant was assayed for endonuclease activity.

EXAMPLE 3

CLONING OF TTH111IR GENE

Figure 3:
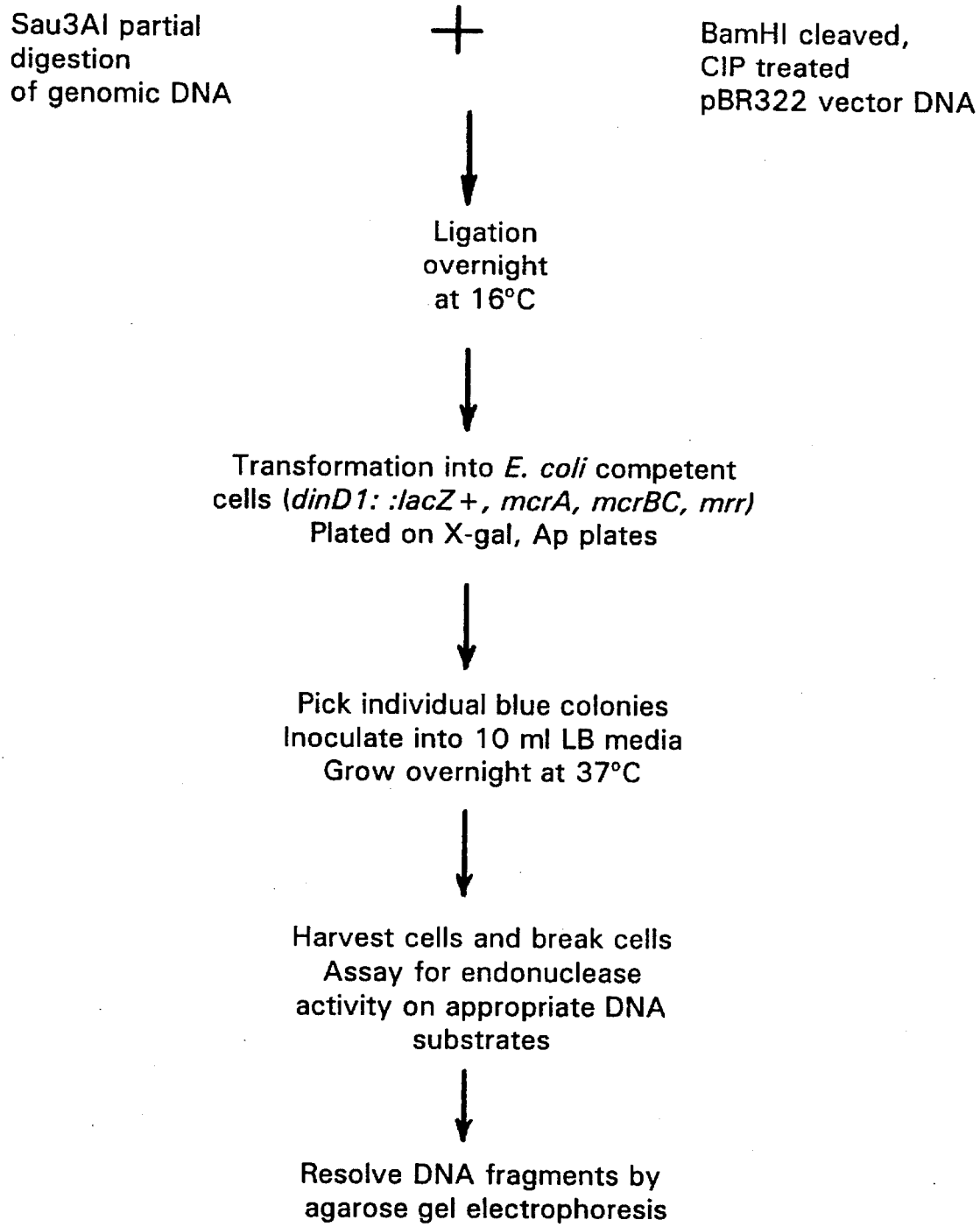
FIG. 3 is a scheme for the cloning of tth 111lR gene, the gene coding for Tth 111l, in *E. coli*.

Genomic DNA was prepared from *Thermus thermophilus* 111 strain which produces Tth111 1 restriction enzyme. Five grams of cells were resuspended in 25 ml of buffer containing 25% sucrose, 50 mM Tris-HCl, pH 8.0. Five ml of 0.5 M EDTA, pH 8.0, and 6 ml of lysozyme (10 mg/ml) were added to the cell suspension. After 10 min incubation at room temperature, 36 ml of lysis buffer (1% Triton X-100, 50 mM Tris-HCl, pH 8.0, 62 mM EDTA) and 5 ml of 10% SDS were added to completely lysed the cells. Proteins were removed by phenol-$CHCl_3$ extraction twice and $CHCl_3$ extraction twice and genomic DNA was precipitated by addition of 1/10 volume of 3.5 M sodium acetate and equal volume of isopropanol and centrifugation at 15,000 g. The DNA pellet was washed with 50 ml of 70% ethanol and dried under vacuum. The DNA was resuspended in 10 ml of TE buffer and dialysed in 2 liters of TE buffer overnight at 4° C. Fifty μg Of genomic DNA was digested with 1 unit, 0.5 unit, 0.25 unit, 0.125 unit of Sau3Al at 37° C. for 30 min. The digested DNA was purified by phenol-$CHCl_3$ extraction twice and $CHCl_3$ extraction twice and ethanol precipitation. Vector pBR322 DNA was linearized by BamHI restriction enzyme and dephosphorylated by calf intestinal alkaline phosphatase (CIP).The vector DNA was purified by phenol-$CHCl_3$ extraction twice and $CHCl_3$ extraction twice and ethanol precipitation. The Sau3Al partially digested genomic DNA was ligated with BamHl-cleaved and CIP-treated pBR322 DNA. The DNA ligation mixture was transformed into *E. coli* ER1992 (dinD1::lacZ, hsdR, mcrA, mcrBC, mrr ) competent cells. Forty blue colonies were found among 8,000 transformants. These forty strains were checked for endonuclease activity. Fourteen strains make Tth111I endonuclease (FIG. 3). Plasmid DNA from Tth111I-producing strains were prepared and subjected to Tth111I restriction digestion. Twelve plasmids were linearized by Tth111I endonuclease, suggesting either methylase gene is not contained in the same fragment or it is not expressed 37° C. Three plasmids were partially resistant to Tth111I, indicating the presence of the cognate methylase gene on the cloned fragment.

EXAMPLE 4

CLONING OF ECOO109IR GENE BY COMBINATION OF METHYLASE SELECTION METHOD AND BLUE COLONY SCREENING METHOD

In this Example, the possibility of combining the methylase selection method and the endonuclease indicator method for cloning of restriction endonuclease gene was tested. Genomic DNA of *E. coli* H709c was prepared as described in Example 2. The DNA was cleaved partially with Sau3Al as described in Example 2 and ligated to pBR322 (BamHI linearized and CIP treated) at 16° C. overnight. The ligation mixture was used to transform E. coli RR1 competent cells. A total of 105 transformants were pooled and inoculated into 500 ml LB medium. The cell culture was shaken overnight at 37° C. Bacterial cells were harvested by centrifugation and resuspended in 20 ml of buffer P1 (100 μg/ml RNAseA, 50 mM Tris-HCl, 10 mM EDTA, pH 8.0). Following addition of 20 ml buffer P2 (200 mM NaOH, 1% SDS) and incubation at room temperature for five min, 20 ml of buffer P3 was added (2.55 M KAc, pH 4.8). The precipitates were removed by centrifugation at 4° C. for 30 min (20,000xg). The supernatant was loaded into two Qiagen midi-columns preequilibrated with buffer QBT (750 mM NaCl, 50 mM MOPS, 15% ethanol, pH 7.0, 0.15% Triton X-100). The plasmid DNA was washed with 20 ml of buffer QC (1 M NaCl, 50 mM MOPS, 15% ethanol, pH 7.0) and eluted with 5 ml of buffer QF (1.25 mM NaCl, 50 mM MOPS, 15% ethanol, pH 8.2). The plasmid DNA was precipitated with equal volume of isopropanol and centrifugation at 4° C. for 30 min. The DNA pellet was washed with 70% ethanol, dried under vacuum, and dissolved in 1 ml of TE buffer. Ten μg of plasmid DNA from the plasmid library was digested with 100 units of EcoO1091 restriction enzyme at 37° C. for three hours. The digested plasmid DNA was used to transform *E. coli* ER1992 (dinD1::lacZ, hsdR, mcrA, mcrBC, mrr) and cells are plated on X-gal plus Ap plates. Fourteen blue colonies were found among 120 transformants. Ten ml of cell culture was made from each of 14 strains and cell extracts prepared (as described in Example 1) to assay for EcoO1091 endonuclease activity on λ DNA substrate. Eight strains were found to make EcoO1091 restriction endonuclease. By combining the methylase selection method and the endonuclease indicator method one could eliminate those clones that only carry methylase gene or lost cleavage sites after challenge but identify those clones that carry endonuclease gene alone or together with the methylase gene.

EXAMPLE 5

CLONING Of A GENE CODING FOR A THERMOSTABLE NUCLEASE

Genomic DNA from strain Thermus filiformis was prepared as described in Example 2. The DNA was cleaved partially with Sau3Al as described in Example 2 and ligated to pBR322 (BarnHi linearized and CIP treated) at 16° C. overnight. The ligation mixture was used to transform *E. coli* ER1992 competent cells and plated on X-gal, Amp plates. A total of 8,000 transformants were obtained from one transformation experiment. Among these transformants, twenty-three blue colonies were found. Ten ml of cell culture were made from each of the 23 blue isolates and cell extracts prepared (as described in Example 2) to assay for DNA nuclease activity on pBR322 DNA substrate. The cell extract from one isolate named Tfi#17 displayed DNA nicking activity on pBR322 double-stranded DNA at 68° C. incubation temperature. To further test the nuclease activity, M13mp18 RF form (double-stranded DNA) and single-stranded form were used as the substrates. Again, the nuclease shows DNA nicking activity on the double-stranded substrate. The single-stranded DNA were degraded with the addition of the nuclease. When double-stranded DNA (lambda DNA or M13 RF form) were incubated with the nuclease for a long period of time (12 hours), the DNA was also degraded. Therefore, we concluded the preferred substrate for the Thermus nuclease is single-strand DNA. We also tested that the nuclease can be used for unidirectional deletion application such as after exonuclease III digestion of double-stranded DNA, the remaining single-stranded DNA can be removed by the Thermus nuclease.

What is claimed is:

1. Isolated DNA coding for the BsoBl restriction endonuclease, wherein the isolated DNA is obtainable from the vector pBsoR1.

2. A recombinant DNA vector comprising a vector into which a DNA segment coding for the BsoBl restriction endonuclease has been inserted.

3. A cloning vector which comprises the isolated DNA of claim 1.

4. A host cell transformed by the cloning vector of claim 3.

5. A method of producing an BsoBl restriction endonuclease comprising culturing a host cell transformed with the vector of claim 3 under conditions suitable for expression of said endonuclease.

* * * * *

UNITED STATES PATENT AND TRADEMARK OFFICE
CERTIFICATE OF CORRECTION

PATENT NO. : 5,492,823
DATED : February 20, 1996
INVENTOR(S) : Xu

It is certified that error appears in the above-indentified patent and that said Letters Patent is hereby corrected as shown below:

Column 1, line 7, replace "*Pst* I" with --*Pst*I--

Column 2, line 20, replace "*Bsu* RI" with --*BsuRI*--.

Column 4, line 10, repalce "50mM" with --50 mM--

Column 4, lines 56, replace "dinA" with --*dinA*--

Column 4, line 58, replace "dinG" with --*dinG*--

Column 4, line 61, replace "(phoA)" with --(*phoA*)--

Column 4, line 63, replace "(lux)" with --(*lux*)--

Column 5, line 60, replace "Kan$^R$" with --Kan$^r$--

Column 6, line 9, replace "FROM" with --FOR--

Column 6, line 45, replace "lacZ$^+$" with --lacZ--

Column 7, line 4, replace "(BsoB1R)" with --(*bso*B1R)--

Column 7, line 32, replace "TcR" with --Tc$^r$--

Column 7, line 48, replace "NH3AC" with --NH4AC--

Column 8, line 16, replace "Bam HI" with --*Bam*HI--

Column 9, line 60, replace "ECO01091R" with --ECO0109IR--

UNITED STATES PATENT AND TRADEMARK OFFICE
CERTIFICATE OF CORRECTION

PATENT NO. : 5,492,823
DATED : February 20, 1996
INVENTOR(S) : Xu

It is certified that error appears in the above-indentified patent and that said Letters Patent is hereby corrected as shown below:

Column 11, line 3, replace "strand" with --stranded--

Cover Page [57], 3rd line, replace "E.coli" with --*E. coli*--

Column 1, line 6, after "1994" insert --, incorporated herein by reference--

Column 1, line 11, replace "BsoB1" with --*Bso*BI--

Column 1, line 27, replace "bacteda" with --bacteria--

Column 1, line 65, replace "EcoR11" with --*Eco*RII--

Column 1, line 66, replace "Hha1I" with --*Hha*II--

Column 1, line 67, replace "Pst" with --*Pst*--

Column 2, line 12, replace "EcoRV" with --*Eco*RV--

Column 2, line 12, replace "aL," with --al.,--

Column 2, line 13, replace "PaeR7" with --*Pae*R7--

Column 2, line 15, replace "Pvu1l" with --*Pvu*II--

Column 2, line 20, replace "Bsu R1" with --*Bsu*RI--

Column 2, line 20, replace "Add." with --Acid.--

UNITED STATES PATENT AND TRADEMARK OFFICE
CERTIFICATE OF CORRECTION

PATENT NO. : 5,492,823
DATED : February 20, 1996
INVENTOR(S) : Xu

It is certified that error appears in the above-indentified patent and that said Letters Patent is hereby corrected as shown below:

Column 2, line 25, replace "BspRl" with --*BspRI*--

Column 2, line 26, replace "Bcnl" with --*BcnI*--

Column 2, line 27, replace "BsuRl" with --*BsuRI*--

Column 2, line 28, replace "Mspl" with --*MspI*--

Column 2, line 35, replace "dinD1::lacZ" with --*dinD1::lacZ*--

Column 2, line 37, replace "dinD1" with --*dinD1*--

Column 2, line 47, replace "mcrA, mcrBC, rnrr" with --*mcrA, mcrBC, mrr*--

Column 2, lines 47-48, replace "dinD1::lacZ" with --*dinD1::lacZ*--

Column 2, line 50, replace "etal" with --et al--

Column 2, line 65, replace "BsoBl" with --*BsoBI*--

Column 3, line 3, replace "BsoBl" with --*BsoBI*--

Column 3, line 7, replace "BsoBl" with --*BsoBI*--

Column 3, line 7-8, replace "stearotherrnophilus" with --*stearothermophilus*--

UNITED STATES PATENT AND TRADEMARK OFFICE
CERTIFICATE OF CORRECTION

PATENT NO. : 5,492,823
DATED : February 20, 1996
INVENTOR(S) : Xu

It is certified that error appears in the above-indentified patent and that said Letters Patent is hereby corrected as shown below:

Column 3, line 9, replace "bsoBIR" with --*bso*BIR--

Column 3, line 10, replace "BsoBl" with --*Bso*BI--

Column 3, line 12, replace "dinD1::lacZ" with --*dinD1::lacZ*--

Column 3, line 14, replace "BsoBl" with --*Bso*BI--

Column 3, line 17, replace "dinD1::lacZ" with --*dinD1::lacZ*--

Column 3, line 18, replace "BsoBl" with --*Bso*BI--

Column 3, line 20, replace "EcoRl, or BamHl" with --*Eco*RI, or *Bam*HI--

Column 3, line 21, replace "E. coli" with --*E. coli*--

Column 3, line 22, replace "BioL" with --*Biol.*--

Column 3, line 27, replace "dinD1::lacZ" with --*dinD1::lacZ*--

Column 3, line 35, replace "BsoBl" with --*Bso*BI--

Column 3, line 37, replace "30°" with --30--

Column 3, line 44, replace "dinD1::lacZ" with --*dinD1::lacZ*--

UNITED STATES PATENT AND TRADEMARK OFFICE
CERTIFICATE OF CORRECTION

PATENT NO. : 5,492,823  
DATED : February 20, 1996  
INVENTOR(S) : Xu

Page 5 of 15

It is certified that error appears in the above-indentified patent and that said Letters Patent is hereby corrected as shown below:

Column 3, line 48, replace "in vivo" with --*in vivo*--

Column 3, line 64, replace "BsoBl" with --*Bso*BI--

Column 3, line 65, replace "Taql" with --*Taq*I--

Column 3, line 65, replace "Tth111l" with --*Tth*111I--

Column 4, line 3, replace "eco01091R" with --eco0109IR--

Column 4, line 8, replace "BsoBl" with --*Bso*BI--

Column 4, line 14, replace "BsoBl" with --*Bso*BI--

Column 4, line 15, replace "BsoBl" with --*Bso*BI--

Column 4, line 18, replace "BsoBl" with --*Bso*BI--

Column 4, line 19, replace "Sau3Al" with --*Sau*3AI--

Column 4, line 21, replace "Barnill" with --*Bam*HI--

UNITED STATES PATENT AND TRADEMARK OFFICE
CERTIFICATE OF CORRECTION

PATENT NO. : 5,492,823                           Page 6 of 15
DATED      : February 20, 1996
INVENTOR(S): Xu It is certified that error appears in the above-indentified patent and that said Letters Patent is hereby corrected as shown below:

Column 4, line 22, replace "tth 1111R" with --*tth*111IR--

Column 4, line 23, replace "Tth 1111" with --*Tth*111IR--

Column 4, line 23, replace "E. coli" with --*E. coli*--

Column 4, line 26, replace "Taq1" with --*Taq*I--

Column 4, line 26, replace "Tth 1111" with --*Tth*111I--

Column 4, line 27, after "*coli.*" insert --This Figure shows the assay of *Taq*I and *Tth*111I endonuclease activity in cell extracts. Lane 1, uncut pBR322 DNA; lane 2, pBR322 cleaved with cell extract containing *Taq*I endonuclease; lane 3, pBR322 cleaved with purified *Taq*I, lane 4, *Bst* EII-cleaved λ DNA size standard; lane 5, uncut λ DNA; lane 6 λ DNA cleaved with cell extract containing *Tth*111I endonuclease; lane 7, λ DNA cleaved with purified *Tth*111I endonuclease. *taq*I and *Tth*111I restriction digestions were performed at 65°C for one hour.--

Column 4, line 34, replace "BsoB1" with --*Bso*BI--

Column 4, line 38, replace "BsoB1" with --*Bso*BI--

Column 4, lines 51-52, replace "hsdR, mcrA, mcrBC, mrr" with --*hsdR, mcrA, mcrBC, mrr*--

UNITED STATES PATENT AND TRADEMARK OFFICE
CERTIFICATE OF CORRECTION

PATENT NO. : 5,492,823  
DATED : February 20, 1996  
INVENTOR(S) : Xu

It is certified that error appears in the above-indentified patent and that said Letters Patent is hereby corrected as shown below:

Column 4, line 58, replace "Bacteriol" with --*Bacteriol.*--

Column 5, line 23, replace "BsoBl" with --*Bso*BI--

Column 5, line 30, replace "replicarive" with --replicative--

Column 5, line 36, replace "BsoBl" with --*Bso*BI--

Column 5, line 37, replace "BsoBl" with --*Bso*BI--

Column 5, line 38, replace "Ava 1" with --*Ava*I--

Column 5, line 40, replace "taql" with --*taq*I--

Column 5, line 40, replace "tth111lR" with --*tth*111IR--
          line 44, replace "stain" with --strain--.
Column 5, line 45, replace "method"," with --method".--

Column 5, line 45, replace "stain E. coli" with --strain *E. coli*--

UNITED STATES PATENT AND TRADEMARK OFFICE
CERTIFICATE OF CORRECTION

PATENT NO. : 5,492,823
DATED : February 20, 1996
INVENTOR(S) : Xu

It is certified that error appears in the above-indentified patent and that said Letters Patent is hereby corrected as shown below:

Column 5, line 45, replace "dinD::lacZ" with --*dinD::lacZ*--

Column 5, line 49, replace "E coli" with --*E. coli*--

Column 5, line 49-51, replace "F-λ-Δ(argF-lac)U169 SupE44 e14⁻ dinD1::Mu d11734 (Kanʳ, LacZ⁺)rfbD1? relA1? endA1 spoT1:thi1 Δ(mcrC-mrr)" with --F⁻λ⁻Δ(argF-lac)U169 SupE44 e14⁻ dinD1::Mu d11734 (Kanʳ, LacZ⁺) rfbD1? relA1? endA1 spoT1?:thi-1 Δ(mcrC-mrr)--

Column 5, line 53, replace "proc" with --*proC*--

Column 5, line 53, replace "argF-lac)U169" with --*argF-lac)U169*--

Column 5, line 57, replace "dinD1" with --*dinD1*--

Column 5, line 58, replace "dinD1" with --*dinD1*--

Column 5, line 59, replace "aL" with --al.,--

UNITED STATES PATENT AND TRADEMARK OFFICE
CERTIFICATE OF CORRECTION

PATENT NO.   : 5,492,823                                      Page 9 of 15
DATED        : February 20, 1996
INVENTOR(S)  : Xu It is certified that error appears in the above-indentified patent and that said Letters Patent is hereby corrected as shown below:

Column 5, line 62, replace "dinD" with --*dinD*--

Column 6, line 8, replace "bsoBIR" with --*bso*BIR--

Column 6, line 9, replace "BsoB1" with --*Bso*BI--

Column 6, line 15, replace "stearotherrnophilus" with --*stearothermophilus*--

Column 6, line 19, replace "10 mm" with --10 min--

Column 6, line 33, replace "Sau3A1" with --*Sau*3AI--

Column 6, line 36, replace "Barnill" with --*Bam*HI--

Column 6, line 41, replace "Sau3A1" with --*Sau*3AI--

Column 6, line 42, replace "BamH1" with --*Bam*HI--

Column 6, lines 45-46, replace "dinD1::lacZ$^+$, hsdR, mcrA, mcrBC, mrr)" with
--*dinD1::lacZ$^+$, hsdR, mcrA, mcrBC, mrr*)--

Column 6, line 48, replace "3-indolyI" with --3-indolyl--

UNITED STATES PATENT AND TRADEMARK OFFICE
CERTIFICATE OF CORRECTION

PATENT NO. : 5,492,823
DATED : February 20, 1996
INVENTOR(S) : Xu

Page 10 of 15

It is certified that error appears in the above-indentified patent and that said Letters Patent is hereby corrected as shown below:

Column 6, line 60, replace "Tds" with --Tris--

Column 6, line 64, replace "BsoB1" with --*Bso*BI--

Column 6, line 66, replace "BsoB1" with --*Bso*BI--

Column 7, line 1, replace both "BsoB1" with --*Bso*BI--

Column 7, line 3, replace "BsoB1" with --*Bso*BI--

Column 7, line 4, replace "pBsoR1" with --p*Bso*R1--

Column 7, line 5, replace "BsoB1" with --*Bso*BI--

Column 7, line 5, replace "pBsoR1" with --p*Bso*R1--

Column 7, line 15, replace "pBsoR1" with --p*Bso*R1--

Column 7, line 16, replace "pBsoR1" with --p*Bso*R1--

Column 7, line 17, replace "pBsoR1" with --p*Bso*R1--

Column 7, line 22, replace "pBsoR1" with --p*Bso*R1--

Column 7, line 26, replace "Ava1" with --*Ava*I--

Column 7, lines 27-28, replace "Ava1 and BsoB1" with --*Ava*I and *Bso*BI--

UNITED STATES PATENT AND TRADEMARK OFFICE
CERTIFICATE OF CORRECTION

PATENT NO. : 5,492,823
DATED : February 20, 1996
INVENTOR(S) : Xu

It is certified that error appears in the above-indentified patent and that said Letters Patent is hereby corrected as shown below:

Column 7, line 29, replace "Pst1" with --*PstI*--

Column 7, line 29, replace "Ava1" with --*AvaI*--

Column 7, line 30, replace "ava1M" with --*AvaIM*--

Column 7, line 30, replace "pAva1RM12" with --p*AvaI*RM12--

Column 7, line 32, replace "ava1M" with --*avaIM*--

Column 7, line 33, replace "dinD::LacZ" with --*dinD::lacZ*--

Column 7, line 34, replace "BsoB1" with --*BsoBI*--

Column 7, line 36, replace "ava1M" with --*avaIM*--

UNITED STATES PATENT AND TRADEMARK OFFICE
CERTIFICATE OF CORRECTION

PATENT NO. : 5,492,823
DATED : February 20, 1996
INVENTOR(S) : Xu

It is certified that error appears in the above-indentified patent and that said Letters Patent is hereby corrected as shown below:

Column 7, line 38, replace "AvaI" with --*Ava*I--

Column 7, line 39, replace "BsoB1" with --*Bso*BI--

Column 7, line 43, replace "Tds" with --Tris--

Column 7, line 56, replace "pBsoR1" with --p*Bso*R1--

Column 7, line 63, replace "TAQIR" with --*TAQI*R--

Column 7, line 66, replace "were, resuspended" with --were resuspended--

Column 8, line 8, replace "1/10volume" with --1/10 volume--

Column 8, line 14, replace "Sau3A1" with --*Sau*3AI--

Column 8, line 21, replace "Sau3A1" with --*Sau*3AI--

Column 8, line 22, replace "BamHI" with --*Bam*HI--

Column 8, lines 24-25, replace "dinD1::lacZ, hsdR, mcrA, mcrBC, mrr" with --*dinD1::lacZ, hsdR, mcrA, mcrBC, mrr*--

UNITED STATES PATENT AND TRADEMARK OFFICE
CERTIFICATE OF CORRECTION

PATENT NO. : 5,492,823
DATED : February 20, 1996
INVENTOR(S) : Xu

It is certified that error appears in the above-indentified patent and that said Letters Patent is hereby corrected as shown below:

```
Column 8, line 34, replace "E coli" with --E. coli--

Column 8, line 43, replace "Taq1" with --TaqI--

Column 8, line 45, replace "Taq1" with --TaqI--

Column 8, line 46, replace "Taq1" with --TaqI--

Column 8, line 48, replace "Taq1" with --TaqI--

Column 8, line 62, replace "1/10volume" with
      --1/10 volume--

Column 9, line 3, replace "Taq1" with --TaqI--

Column 9, line 5, replace "Taq1" with --TaqI--

Column 9, line 17, replace "TTH111IR" with
      --TTH111IR--

Column 9, line 19, replace "Tth111 1" with
      --Tth111I--

Column 9, line 34, replace "Of" with --of--

Column 9, line 35, replace "Sau3A1" with --Sau3AI--

Column 9, line 38, replace "BamH1" with --BamHI--

Column 9, line 42, replace "Sau3A1" with --Sau3AI--

Column 9, line 43, replace "BamH1" with --BamHI--
```

UNITED STATES PATENT AND TRADEMARK OFFICE
CERTIFICATE OF CORRECTION

PATENT NO. : 5,492,823　　　　　　　　　　　　　Page 14 of 15
DATED : February 20, 1996
INVENTOR(S) : Xu It is certified that error appears in the above-indentified patent and that said Letters Patent is hereby corrected as shown below:

Column 9, lines 45-46, replace "dinD1::lacZ, hsdR, mcrA, mcrBC, mrr" with --*dinD1::lacZ, hsdR, mcrA, mcrBC, mrr*--

Column 9, line 49, replace "Tth1111" with --*Tth*111I--

Column 9, line 49, replace "Tth1111" with --*Tth*111I--

Column 9, line 50, replace "Tth1111" with --*Tth*111I--

Column 9, line 52, replace "Tth1111" with --*Tth*111I--

Column 9, line 54, replace "Tth1111" with --*Tth*111I--

Column 10, line 3, replace "Sau3A1" with --*Sau*3AI--

Column 10, line 4, replace "BamH1" with --*Bam*HI--

Column 10, line 5, replace "E. coli" with --*E. coli*--

Column 10, line 26, replace "Ecoo1091" with --*Eco*0109I--

Column 10, lines 28-29, replace "dinD1::lacZ, hsdR, mcrA mcrBC, mrr" with --*dinD1::lacZ, hsdR, mcrA mcrBC, mrr*--.

UNITED STATES PATENT AND TRADEMARK OFFICE
CERTIFICATE OF CORRECTION

PATENT NO. : 5,492,823
DATED : February 20, 1996
INVENTOR(S) : Xu

It is certified that error appears in the above-indentified patent and that said Letters Patent is hereby corrected as shown below:

Column 10, line 33, replace "Eco01091" with --*Eco*0109I--

Column 10, line 34, replace "Eco01091" with --*Eco*0109I--

Column 10, line 47, replace "Thermus filiforrnis" with --*Thermus filiformis*--

Column 10, line 49, replace "Sau3A1" with --*Sau*3AI--

Column 10, line 50, replace "BarnHi" with --*Bam*HI--

Column 11, line 10, replace "BsoB1" with --*Bso*BI--

Column 11, line 12, replace "pBsoR1" with --p*Bso*R1--

Column 12, line 2, replace "BsoB1" with --*Bso*BI--

Column 12, line 8, replace "BsoB1" with --*Bso*BI--

Signed and Sealed this

Twentieth Day of August, 1996

*Attest:*

BRUCE LEHMAN

*Attesting Officer*    *Commissioner of Patents and Trademarks*